(12) United States Patent
Mitra et al.

(10) Patent No.: US 7,226,928 B2
(45) Date of Patent: Jun. 5, 2007

(54) METHODS FOR THE TREATMENT OF PERIODONTAL DISEASE

(75) Inventors: Sumita B. Mitra, West St. Paul, MN (US); Charles E. Shelburne, Brooklyn Park, MN (US); Mark A. Tomai, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/479,109

(22) PCT Filed: Jun. 14, 2002

(86) PCT No.: PCT/US02/18944

§ 371 (c)(1),
(2), (4) Date: Nov. 24, 2003

(87) PCT Pub. No.: WO02/102377

PCT Pub. Date: Dec. 27, 2002

(65) Prior Publication Data

US 2004/0235881 A1 Nov. 25, 2004

(51) Int. Cl.
*A61K 31/535* (2006.01)
*A61K 31/44* (2006.01)

(52) U.S. Cl. ............. 514/293; 514/228.5; 514/253.03; 544/60; 544/361; 544/364; 548/82

(58) Field of Classification Search ................ 514/293, 514/228.5, 253.03; 544/60, 361, 364; 546/82
See application file for complete search history.

(56) References Cited

U.S. PATENT DOCUMENTS

| | | | |
|---|---|---|---|
| 3,314,941 A | 4/1967 | Littell et al. | |
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster | |
| 5,268,376 A | 12/1993 | Gerster | |
| 5,346,905 A | 9/1994 | Gerster | |
| 5,352,784 A | 10/1994 | Nikolaides et al. | |
| 5,367,076 A | 11/1994 | Gerster | |
| 5,389,640 A | 2/1995 | Gerster et al. | |
| 5,395,937 A | 3/1995 | Nikolaides et al. | |
| 5,446,153 A | 8/1995 | Llindstrom et al. | |
| 5,482,936 A | 1/1996 | Lindstrom | |
| 5,494,916 A | 2/1996 | Lindstrom et al. | |
| 5,525,612 A | 6/1996 | Gerster | |
| 5,693,811 A | 12/1997 | Lindstrom | |
| 5,741,908 A | 4/1998 | Gerster et al. | |
| 5,756,747 A | 5/1998 | Gerster et al. | |
| 5,854,257 A | 12/1998 | Armitage et al. | |
| 5,939,090 A | 8/1999 | Beaurline et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,194,425 B1 | 2/2001 | Gerster et al. | |
| 6,200,592 B1 | 3/2001 | Tomai et al. | |
| 6,245,766 B1 | 6/2001 | Watsky | |
| 6,245,776 B1 * | 6/2001 | Skwierczynski et al. | ..... 514/293 |
| 6,331,539 B1 * | 12/2001 | Crooks et al. | ........... 514/228.5 |
| 6,376,669 B1 | 4/2002 | Rice et al. | |
| 6,451,810 B1 | 9/2002 | Coleman et al. | |
| 6,486,168 B1 * | 11/2002 | Skwierczynski et al. | ..... 514/293 |
| 6,518,265 B1 | 2/2003 | Kato et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |
| 6,573,273 B1 | 6/2003 | Crooks et al. | |
| 6,610,319 B2 | 8/2003 | Tomai et al. | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |

(Continued)

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 9-255926 | 3/1999 |
| JP | 11-222432 | 8/1999 |

(Continued)

OTHER PUBLICATIONS

Bernstein, J of Infectious diseases, vol. 183(6), pp. 844-849, 2001.*
Diaz-Arrastia, Clinical Cancer Research, 7(10), pp. 3031-3033, 2001.*
Spruance, J of Infectious Diseases, 184(2), pp. 196-200, 2001.*
Soria, Chemical Abstracts 137:163261, abstract of Therapeutics, 38(10), 476-481, 2000.*
Bishop, J of Immunology, 165(10), 5552-5557, 2000.*
Wozniak, et al, "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

(Continued)

*Primary Examiner*—D. Margaret Seaman
(74) *Attorney, Agent, or Firm*—Ted K. Ringsred (57) ABSTRACT

The disclosure provides methods for the treatment and prevention of periodontal disease. In preferred embodiments, the invention provides for local treatment of periodontal tissues with a pharmaceutical composition including an immune response modifier (IRM) selected from the group of immune response modifiers comprising imidazoquinoline amines, imidazopyridine amines, 6,7-fused cycloalkylimidazopyridine amines, imidazonaphtyridine amines, oxazoloquinoline amines, thiazoloquinoline amines and 1,2-bridged imidazopyridine amines.

7 Claims, 4 Drawing Sheets

U.S. PATENT DOCUMENTS

| | | |
|---|---|---|
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,894,060 B2 * | 5/2005 | Slade .................. 514/293 |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0110840 A1 | 8/2002 | Tomai et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0161797 A1 | 8/2003 | Miller et al. |
| 2003/0199538 A1 | 10/2003 | Skwierczynski et al. |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |

FOREIGN PATENT DOCUMENTS

| | | |
|---|---|---|
| JP | 2000-247884 | 9/2000 |
| WO | WO 00/76505 | 12/2000 |
| WO | WO 00/76518 | 12/2000 |
| WO | WO 02/07725 | 1/2002 |
| WO | WO 02/36592 | 5/2002 |
| WO | WO 03/103584 | 12/2003 |

OTHER PUBLICATIONS

Brennan, et al., "Automated Bioassay of Interferons in Micro-test Plates", *Biotechniques*, Jun./Jul. 78, 1983.

Testerman, et al., "Cytokine Induction by the Immunomodulators Imiquimod and S-27609", *Journal of Leukocyte Biology*, vol. 58, pp. 365-372, Sep. 1995.

Bachman, et al, "Synthesis of Substituted Quinolylamines. Derivatives of 4-Amino-7-Chloroquinoline", *J. Org. Chem*, 15, pp. 1278-1284 (1950).

Jain, et al, "Chemical and Pharmacological Investigations of Some ω-Substituted Alkylamino-3-aminopyridines", *J. Med. Chem.*, 11, pp. 87-92 (1968).

Baranov, et al., *Chem. Abs.* 85, 94362, (1976).

Berényi, et al, "Ring Transformation of Condensed Dihydro-astriazines", *J. Heterocyclic Chem.*, 18, pp. 1537-1540 (1981).

Chollet, et al, "Development of a Topically Active Imiquimod Formulation", *Pharmaceutical Development and Technology*, 4(1), pp. 35-43 (1999).

Izumi, et al., "1$H$-Imidazo[4,5-c]quinoline Derivatives as Novel Potent TNF-α Suppressors: Synthesis and Structure-Activity Relationship of 1-, 2- and 4-Substituted 1$H$-imidazo[4,5-c]pyridines", *Bioorganic & Medicinal Chemistry*, 11, pp. 2541-2550 (2003).

Kornman, Kenneth S., "Host Modulation as a Therapeutic Strategy in the Treatment of Periodontal Disease", *Clinical Infectious Diseases*, vol. 28, No. 3, 520-526, Mar. 1999.

Zambon, J.J., "Periodontal Disease: Microbial Facors", *Ann. Peridontol*, vol. 1, pp. 879-825, 1996.

Beck, et al, "Dental Infections and Atherosclerosis", *American Heart Journal*, 13, pp. 528-533, 1999.

Loesche, et al, Treatment Paradigms in Pariodontal Disease, *Compen. Contin. Educ. Dental*, vol. 18 (3), p p. 221-226 and 228-230, 1997.

Page, et al, "Advances in the Pathogenesis of Periodontitis: Summary of Developments, Clinical Implications and Future Directions", *Periodontology 2000*, vol. 14, 216-248, 1997.

Mathur, et al, "Cell-Mediated, Immune System Regulation in Periodontal Disease", *Critical Rev. Oral. Bio. Med.*, vol. 8, pp. 76-89, 1997.

Seymour G. J. et al, "Cellular Immunity and Hypersensitivity as Components of Periodontal Destruction", *Oral Dis.*, vol. 2 (1), pp. 76-101, 1996.

Bartova, et al, "TH1 and TH2 Cytokine Profile in Patients with Earlyonset Periodontitis and their Healthy Siblings", *Mediators Inflamm.*, vol. 9(2), pp. 115-120, 2000.

Assuma, et al, "IL-1 and TNF Antagonists Inhibit the Inflammatory Response and Bone Loss in Experimental Periodontitis", *Journal of Immunology*, vol. 160, pp. 403-409, 2000.

Takeichi, et al, "Cytokine Profiles of T-Lymhocytes from Gingivaltissues with Pathological Pocketing", *J. Dent. Res.*, vol. 79(8), pp. 1548-1555, Aug. 2000.

Wagner, et al, "Modulation of TH1 and TH2 Cytokine Production with the Immune Response Modifiers, R-848 and Imiquimod", *Cellular Immunology*, vol. 191, pp. 10-19, 1999.

* cited by examiner

METHODS FOR THE TREATMENT OF PERIODONTAL DISEASE

FIELD OF THE INVENTION

The invention is directed to methods for the treatment or prevention of periodontal conditions. Specifically the invention includes the novel use of immune response modifier compounds to treat or prevent periodontal disease. Preferred immune response modifiers are selected from the group of immune response modifiers comprising imidazoquinoline amines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines.

BACKGROUND OF THE INVENTION

Periodontal disease or periodontitis is an inflammatory disease that results in the destruction of both the hard and soft tissues supporting the teeth and has recently been hypothesized as a risk factor for cardiovascular disease. Beck et al. "Dental Infections and atherosclerosis," *American Heart Journal* 13:S528–533 (1999). It is estimated that over 10 million people in the United States are currently being treated for the more serious forms of this disease, with approximately 8 billion dollars spent for treatment each year.

Clinically, periodontitis is an inflammation of the periodontium and results in inflammation of the gingiva and may result in resorption of alveolar bone and recession of the gingiva Recession of the gingiva can lead to exposure of the periodontal ligament allowing microorganisms to invade and destroy the ligament.

Infection by a few essential species of bacteria is important in initiating the host inflammatory response that is responsible for the tissue destruction and ultimate loss of teeth. Zambon, J. J., "Periodontal Disease, Microbial Factors," *Ann. Periodontol.*, 1:879–825 (1996). The major pathogens associated with the disease have been identified and include *Porphyromonas gingivalis, Bacteroides forsythus* and *Actitiobacillus actinomycetemcomitans*. Although essential to the pathogenesis, bacteria alone are insufficient to cause the disease. Host factors such as hereditary predisposition and environmental factors such as smoking are believed to equally effect disease occurrence and severity of outcome.

Forms of periodontitis include early onset periodontitis (EOP), chronic adult periodontitis (AP), and refractory periodontitis (RP). Localized juvenile periodontitis is a form of EOP which occurs in otherwise seemingly healthy adolescents and is associated with infection by *A. actinomycetemcomitans*. "Chronic adult periodontitis" is commonly associated with the presence of *B. forsythus, P. gingivalis*, many gram-negative asaccharolytic rods, and oral spirochetes. It typically occurs in patients over 35 years of age. Clinically, it resembles acute necrotizing ulcerative gingivitis imposed on rapidly progressive periodontitis. Patients may lose 9 to 12 mm of gingival attachment in as little as six months.

Current treatment for periodontal disease is almost exclusively mechanical and surgical in nature most frequently including scaling and root planing to remove calculus deposits. However, the mechanical treatments do not affect the underlying cause of disease. Antibiotics have also been used as an adjunct therapy, Loesche et al, "Treatment paradigms in periodontal disease", *Compend. Contin. Educ Dental,* 18(3):221–6, 228–30 (1997). Unfortunately, results have been disappointing because the antibiotic may not eliminate the bacteria responsible for the inflammatory component, and patients are subject to re-infection.

Accordingly, there is a continuing need for new and effective treatment and preventive measures for periodontal disease. The present invention is directed to this need.

SUMMARY OF THE INVENTION

The present invention provides methods for treating or preventing a periodontal condition comprising administering a therapeutically effective amount of an immune response modifier (IRM) compound directly to periodontal tissue in a patient affected by the periodontal condition. In preferred embodiments the IRM compound is selected from the group comprising imidazoquinoline amines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines.

DETAILED DESCRIPTION

The present disclosure provides methods for treatment or prevention of an oral condition, such as periodontal disease, using an immune response modifier (IRM) compound. As used herein, "immune response modifier compound", means a compound which induces the production of one or more cytokines, e.g., Interferon ($\alpha$), Tumor Necrosis Factor, and Interleukin-12, from hematopoietec cells including dendritic cells and/or monocyte/macrophages. Examples of such compounds include the CpG oligonueleotides, lipopolysaccharides, polyinosic:polycytidylic acid complexes, and polypeptides and proteins know to induce cytokine production from dendritic cells and/or monocyte/macrophages.

In preferred embodiments, the IRM compound is selected from the group comprising imidazoquinoline amines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines. Methods for preparing such IRMs and pharmaceutical compositions containing them are disclosed in, for example, U.S. Pat. Nos. 4,689,338; 5,389,640; 5,268, 376; 4,929,624; 5,266,575; 5,352,784; 5,494,916; 5,482, 936; 5,346,905; 5,395,937; 5,238,944; 5,525,612;,5,175, 296; 5,693,811; 5,741,908; 5,939,090; 6,110,929; 4,988, 815; 5,376,076; 6,194,425; 6,245,776; and 6,331,539; and PCT Publications WO 00/76505 and WO 00/76518. The entire disclosure of each of these patents and patent applications is incorporated herein by reference.

Figure 1:
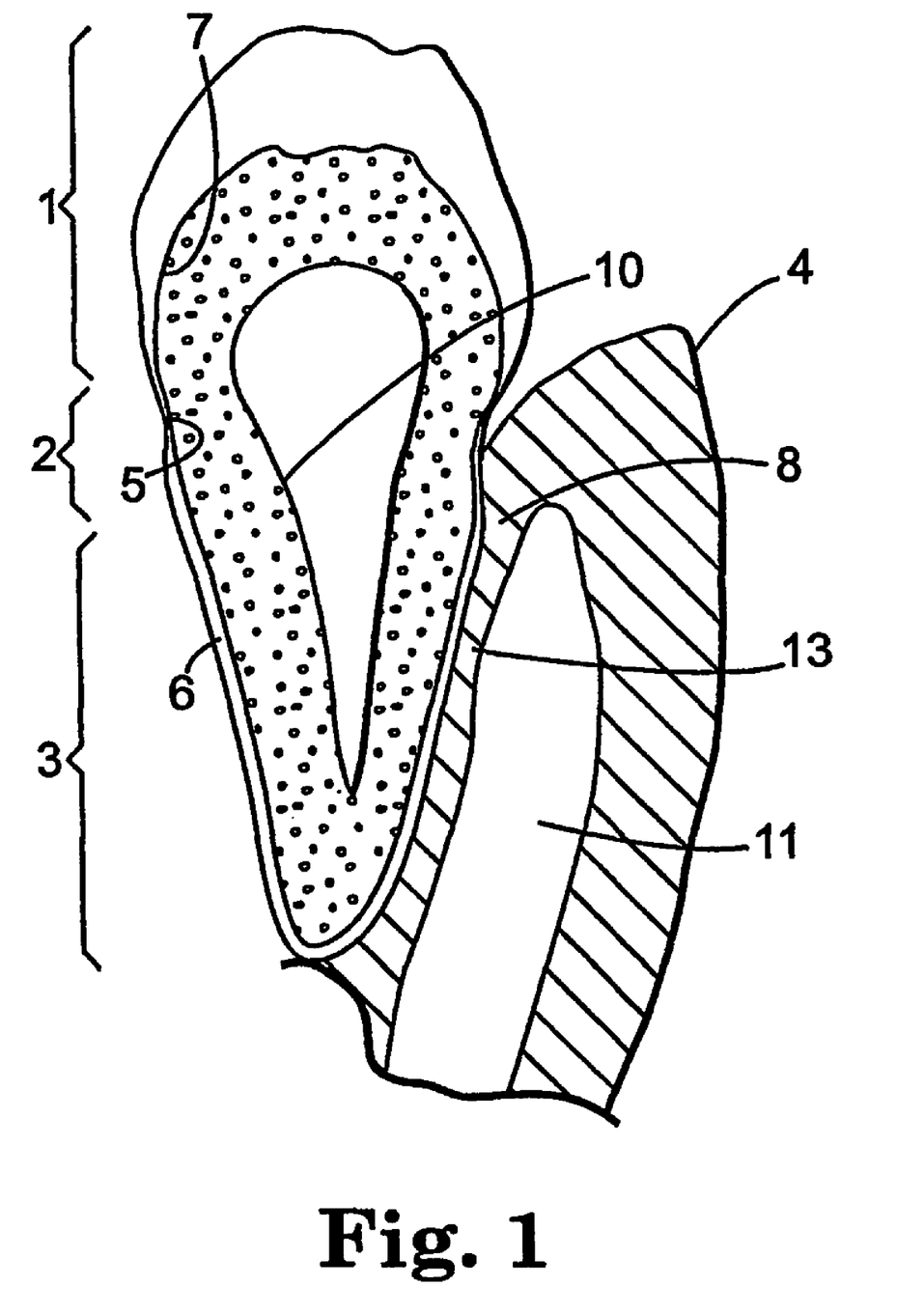
FIG. 1 is a diagram illustrating periodontal anatomy.

As used herein, "periodontitis" is an inflammation or degeneration, or both; of the dental periodontium, alveolar bone, cementum, and adjacent gingival tissue. Referring to FIG. 1, by way of review, each tooth consists of three parts, a crown 1, neck 2 and root 3. The crown 1 is the part of the tooth that projects above the gingiva 4 and occludes with one or more other teeth in the opposite jaw. The neck 2 is the part of the tooth between the crown 1 and the root 3. The cemento-enamel junction (CEJ) 5 is the location where the cementum 6 of the root 3 and enamel 7 of the crown 1 meet. The root 3 is fixed in the tooth socket 8, or "alveolus". Most of the tooth is composed of dentin 10 that is covered by enamel 7 over the crown 1 and cementum 6 over the root 3. The cementum 6 over the root 3 is attached to the alveolar bone 11 by periodontal ligament 13 to form a fibrous joint between the tooth and its alveolus 8.

Thus, as used herein, "periodontal tissues" are the tissues surrounding and supporting a tooth and include the periodontal ligament, alveolar bone and gingiva. A "periodontal pocket" is a pathologically induced space extending below the cemento-enamel junction (CEJ) and resulting from break down of the alveolar bone and/or periodontal ligament.

The inflammatory nature of periodontitis is not yet fully understood, although a general model has been advanced, Page et al., "Advances in the pathogenesis of periodontitis: summary of developments, clinical implications and future directions", *Periodontology* 2000, 14:216–248 (1997). One hypothesis is that the normal immune response against the initiating bacteria, which would prevent the bacteria from causing disease, has been altered and becomes not just in effective but contributory to the disease process, Mathur et al., "Cell-mediated immune system regulation in periodontal disease," *Critical Rev. Oral. Bio. Met.*, 8:76–89 (1997). According to this hypothesis, in patients with minimal or no periodontal disease, the immune response is skewed towards a TH1 immune response, which is generally involved with controlling viruses and tumors. In patients with progressive periodontal disease, the immune response pathway is skewed towards a Th2 response, characterized by activation of B cells to secrete antibodies. It is believed that the antibody response is ineffective against the bacteria, is usually of short duration, and does not lead to immune "memory". In addition, cytokines that are secreted by TH2 cells can activate inappropriate host tissue remodeling enzymes that contribute to the destruction of the connective tissue that holds the teeth to the jaw, and enzymes that cause the resorption of the alveolar bone around the teeth.

Another report sets forth a model of periodontal disease based on the T-cell dichotomy characterized by a higher proportion of IL-4 producing cells in periodontitis tissues, and hypothesize a role for Th2 cells in progressive lesions of the disease, Seymour G. J. et al., "Cellular immunity and hypersensitivity as components of periodontal destruction," *Oral Dis.*, 2(1):96–101 (1996). This report has been recently supported by work by Bartova et al., "TH1 and TH2 cytokine profile in patients with early onset periodontitis and their healthy siblings," *Mediators Inflamm.*, 2(2):115–20 (2000).

A different hypothesis that has been advanced is that the TH1 response, which activates a number of typical cytokines, can result in bone resorption as a result of osteoclast activation. Assuma et al., "IL-1 and TNF antagonists inhibit the inflammatory response and bone loss in experimental periodontitis", *J. of Immunology*, 160:403–409 (1998).

In another report, a cumulative cytokine profile has been observed in periodontitis consistent with the predominance of TH1-type cells, in pathological tissues and with TH2-type cells, when present, being up-regulated under appropriate stimulation. Takeichi et al., "Cytokine profiles of T-lymphocytes from gingival tissues with pathological pocketing," *J.*

*Dent. Res.*, 79(8):1548–55 (August 2000). Both CD4 and CD8+ lymphocytes were shown to express TH1- and TH2-type cytokine messages.

In sum, the foregoing reports emphasize the relative lack of agreement on the mechanisms responsible for periodontal disease pathogenesis, and the lack of consensus for any medicinal approach to disease management.

Many imidazoquinoline amine, imidazopyridine amine, 6,7-fused cycloalkylimidazopyridine amine, imidazonaphthyridine amines, oxazoloquinoline amines, thiazoloquinoline amines and 1,2-bridged imidazoquinoline amine compounds have demonstrated potent immunomodulating, antiviral and antitumor (including anticancer) activity, and have also been shown to be useful as vaccine adjuvants to enhance protective immune system response to vaccines. Recently, it has been found that many of these IRM compounds can inhibit TH2 immune responses, as well as enhance TH1 immune responses. See eg. U.S. Pat. No. 6,039,969, the entire disclosure of which is incorporated herein by reference.

Although the immunology of periodontal disease remains controversial the inventors have now discovered that treatment with immune response modifying compounds may benefit patients with periodontitis and treat the underlying infection. Specifically, treatment with IRM compounds can reduce the destruction of the alveolar bone or periodontal ligament. If treatment is administered at an appropriate time before destruction of periodontal tissues begins, the invention can also be used to modulate the patient's immune response to effectively prevent clinical signs of periodontal disease. Thus the IRM compositions can have both therapeutic and prophylactic value.

A "patient" includes humans and animals

A pharmaceutical composition useful in the method of the invention includes an immune response modifier (IRM) compound. Preferred compositions include compounds selected from the group of immune response modifiers comprising imidazoquinoline amines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines.

Preferred immune response modifier compounds include 1H-imidazo[4,5-c]quinolin-4-amines defined by one of Formulas I–V below:

I wherein $R_{11}$ is selected from the group consisting of alkyl of one to ten carbon atoms, hydroxyalkyl of one to six carbon atoms, acyloxyalkyl wherein the acyloxy moiety is alkanoyloxy of two to four carbon atoms or benzoyloxy, and the alkyl moiety contains one to six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that if said benzene ring is substituted by two of said moieties, then said moieties together contain no more than six carbon atoms;

$R_{21}$ is selected from the group consisting of hydrogen, alkyl of one to eight carbon atoms, benzyl (phenyl)ethyl and phenyl, the benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that when the benzene ring is substituted by two of said moieties, then the moieties together contain no more than six carbon atoms; and each $R_1$ is independently selected from the group consisting of alkoxy of one to four carbon atoms, halogen, and alkyl of one to four carbon atoms, and n is an integer from 0 to 2, with the proviso that if n is 2, then said $R_1$ groups together contain no more than six carbon atoms;

II wherein $R_{12}$ is selected from the group consisting of straight chain or branched chain alkenyl containing two to ten carbon atoms and substituted straight chain or branched chain alkenyl containing two to ten carbon atoms, wherein the substituent is selected from the group consisting of straight chain or branched chain alkyl containing one to four carbon atoms and cycloalkyl containing three to six carbon atoms; and cycloalkyl containing three to six carbon atoms substituted by straight chain or branched chain alkyl containing one to four carbon atoms; and $R_{22}$ is selected from the group consisting of hydrogen, straight chain or branched chain alkyl containing one to eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to four carbon atoms, straight chain or branched chain alkoxy containing one to four carbon atoms, and halogen, with the proviso that when the benzene ring is substituted by two such moieties, then the moieties together contain no more than six carbon atoms; and each $R_2$ is independently selected from the group consisting of straight chain or branched chain alkoxy containing one to four carbon atoms, halogen, and straight chain or branched chain alkyl containing one to four carbon atoms, and n is an integer from zero to 2, with the proviso that if n is 2, then said $R_2$ groups together contain no more than six carbon atoms;

III wherein ;

$R_{23}$ is selected from the group consisting of hydrogen, straight chain or branched chain alkyl of one to eight carbon atoms, benzyl (phenyl)ethyl and phenyl, the benzyl, (phenyl)ethyl or phenyl substituent being optionally substituted on the benzene ring by one or two moieties independently, selected from the group consisting of straight chain or branched chain alkyl of one to four carbon atoms, straight chain or branched chain alkoxy of one to four carbon atoms, and halogen, with the proviso that when the benzene ring is substituted by two such moieties, then the moieties together contain no more than six carbon atoms; and each $R_3$ is independently selected from the group, consisting of straight chain or branched chain alkoxy of one to four carbon atoms, halogen, and straight chain or branched chain alkyl of one to four carbon atoms, and n is an integer from zero to 2, with the proviso that if n is 2, then said $R_3$ groups together contain no more than six carbon atoms;

IV wherein $R_{14}$ is —$CHR_xR_y$, wherein $R_y$ is hydrogen or a carbon-carbon bond, with the proviso that when $R_y$ is hydrogen $R_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to four carbon atoms;

$R_{24}$ is selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen; and

$R_4$ is selected from the group consisting of hydrogen, straight chain or branched chain alkoxy containing one to four carbon atoms, halogen, and straight chain or branched chain alkyl containing one to four carbon atoms;

wherein

R$_{15}$ is selected from the group consisting of: hydrogen; straight chain or branched chain alkyl containing one to ten carbon atoms and substituted straight chain or branched chain alkyl containing one to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; straight chain or branched chain alkenyl containing two to ten carbon atoms and substituted straight chain or branched chain alkenyl containing two to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

R$_{25}$ is wherein

R$_S$ and R$_T$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen;

X is selected from the group consisting of alkoxy containing one to four carbon atoms, alkoxyalkyl wherein the alkoxy moiety contains one to four carbon atoms and the alkyl moiety contains one to four carbon atoms, hydroxyalkyl of one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, alkylthio of one to four carbon atoms; and R$_5$ is selected from the group consisting of hydrogen, straight chain or branched chain alkoxy containing one to four carbon atoms, halogen and straight chain or branched chain alkyl containing one to four carbon atoms;

and a pharmaceutically acceptable salt of any of the foregoing.

Preferred 6,7 fused cycloalkylimidazopyridine amine IRM compounds are defined by Formula VI below:

wherein m is 1, 2, or 3;

R$_{16}$ is selected from the group consisting of hydrogen; cyclic alkyl of three, four, or five carbon atoms; straight chain or branched chain alkyl containing one to ten carbon atoms and substituted straight chain or branched chain alkyl containing one to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; fluoro- or chloroalkyl containing from one to ten carbon atoms and, one or more fluorine or chlorine atoms; straight chain or branched chain alkenyl containing two to ten carbon atoms and substituted straight chain or branched chain alkenyl containing two to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms, with the proviso that any such alkyl, substituted alkyl alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

and —CHR$_x$R$_y$, wherein;

R$_y$ is hydrogen or a carbon-carbon bond, with the proviso that when R$_y$ is hydrogen R$_x$ is alkoxy of one to four carbon atoms, hydroxyalkoxy of one to four carbon atoms, 1-alkynyl of two to ten carbon atoms; tetrahydropyranyl, alkoxyalkyl wherein the alkoxy moiety contains one to four carbon atoms and the alkyl moiety contains one to four carbon atoms, 2-, 3-, or 4-pyridyl; and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to four carbon atoms, $R_{26}$ is selected from the group consisting of hydrogen, straight chain or branched chain alkyl containing one to eight carbon atoms, straight chain or branched chain hydroxyalkyl containing one to six carbon atoms, morpholinoalkyl, benzyl, (phenyl)ethyl and phenyl, the benzyl, (phenyl)ethyl or phenyl substituent being optionally substituted on the benzene ring by a moiety selected from the group consisting of methyl, methoxy, and halogen; and

—$C(R_S)(R_T)(X)$ wherein $R_S$ and $R_T$ are independently selected from the group consisting of one to four carbon atoms, phenyl, and substituted phenyl wherein the substituent is selected from the group consisting of alkyl of one to four carbon atoms, alkoxy of one to four carbon atoms, and halogen;

X is selected from the group consisting of alkoxy containing one to four carbon atoms, alkoxyalkyl wherein the alkoxy moiety contains one to four carbon atoms and the alkyl moiety contains one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, alkylthio of one to four carbon atoms, and morpholinoalkyl wherein the alkyl moiety contains one to four carbon atoms, and $R_6$ is selected from the group consisting of hydrogen, fluoro, chloro, straight chain or branched chain alkyl containing one to four carbon atoms, and straight chain or branched chain fluoro- or chloroalkyl containing one to four carbon atoms and at least one fluorine or chlorine atom;

and pharmaceutically acceptable salts thereof.

Preferred imidazopyridine amine IRM compounds are defined by Formula VII below:

VII wherein

$R_{17}$ is selected from the group consisting of hydrogen; —$CH_2R_W$ wherein $R_W$ is selected from the group consisting of straight chain, branched chain, or cyclic alkyl containing one to ten carbon atoms, straight chain or branched chain alkenyl containing two to ten carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, and phenylethyl; and —$CH=CR_ZR_Z$ wherein each $R_Z$ s independently straight chain, branched chain, or cyclic alkyl of one to six carbon atoms;

$R_{27}$ is selected from the group consisting of hydrogen, straight chain or branched chain alkyl containing one to eight carbon atoms, straight chain or branched chain hydroxyalkyl containing one to six carbon atoms, alkoxy- alkyl wherein the alkoxy moiety contains one to four carbon atoms and the alkyl moiety contains one to six carbon atoms, benzyl, (phenyl)ethyl and phenyl, the benzyl, (phenyl)ethyl or phenyl substituent being optionally substituted on the benzene ring by a moiety selected from the group consisting of methyl, methoxy, and halogen; and morpholinoalkyl wherein the alkyl moiety contains one to four carbon atoms;

$R_{67}$ and $R_{77}$ are independently selected from the group consisting of hydrogen and alkyl of one to five carbon atoms, with the proviso that $R_{67}$ and $R_{77}$ taken together contain no more than six carbon atoms, and with the further proviso that when $R_{77}$ is hydrogen then $R_{67}$ is other than hydrogen and $R_{27}$ is other than hydrogen or morpholinoalkyl, and with the further proviso that when $R_{67}$ is hydrogen then $R_{77}$ and $R_{27}$ are other than hydrogen;

and pharmaceutically acceptable salts thereof.

Preferred 1,2-bridged imidazoquinoline amine IRM compounds are defined by Formula VIII below:

VIII wherein

Z is selected from the group consisting of:

—$(CH_2)_p$— wherein p is 1 to 4;

—$(CH_2)_a$—$C(R_DR_E)(CH_2)_b$—, wherein a and b are integers and a+b is 0 to 3, $R_D$ is hydrogen or alkyl of one to four carbon atoms, and $R_E$ is selected from the group consisting of alkyl of one to four carbon atoms, hydroxy, —$OR_F$ wherein $R_F$ is alkyl of one to four carbon atoms, and —$NR_GR'_G$ wherein $R_G$ and $R'_G$ are independently hydrogen or alkyl of one to four carbon atoms; and —$(CH_2)_a$—(Y)—$(CH_2)_b$— wherein a and b are integers and a+b is 0 to 3, and Y is O, S, or —$NR_J$— wherein $R_J$ is hydrogen or alkyl of one to four carbon atoms;

and wherein q is 0 or 1 and $R_8$ is selected from the group consisting of alkyl of one to four carbon atoms, alkoxy of one to four carbon atoms, and halogen, and pharmaceutically acceptable salts thereof.

Suitable thiazolo- and oxazolo-quinolinamine and pyridinamine compounds include compounds of Formula IX:

IX wherein:

$R_{19}$ is selected from the group consisting of oxygen, sulfur and selenium;

$R_{29}$ is selected from the group consisting of
-hydrogen;

-alkyl;
-alkyl-OH;
-haloalkyl;
-alkenyl;
-alkyl-X-alkyl;
-alkyl-X-alkenyl;
-alkenyl-X-alkyl;
-alkenyl-X-alkenyl;
-alkyl-N($R_{59}$)$_2$;
-alkyl-$N_3$;
-alkyl-O—C(O)—N($R_{59}$)$_2$;
-heterocyclyl;
-alkyl-X-heterocyclyl;
-alkenyl-X-heterocyclyl,
-aryl;
-alkyl-X-aryl;
-alkenyl-X-aryl;
-heteroaryl;
-alkyl-X-heteroaryl; and
-alkenyl-X-heteroaryl;
$R_{39}$ and $R_{49}$ are each independently:
-hydrogen;
-X-alkyl;
-halo;
-haloalkyl;
—N($R_{59}$)$_2$;
or when taken together, $R_{39}$ and $R_{49}$ form a fused aromatic, heteroaromatic, cycloalkyl or heterocyclic ring;
X is selected from the group consisting of —O—, —S—, —N$R_{59}$—, —C(O)—, —C(O))O—, —OC(O)—, and a bond; and
each $R_{59}$ is independently H or $C_{1-8}$alkyl;
and pharmaceutically acceptable salts thereof.

Suitable imidazonaphthyridine and tetrahydroimidazonaphthyridine IRM compounds are those of Formulae X and XI below:

X wherein
A is =N—CR=CR—CR=; =CR—N=CR—CR=; =CR—CR=N—CR=; or =CR—CR=CR—N=;
$R_{110}$ is selected from the group consisting of:
-hydrogen;
—$C_{1-20}$ alkyl or $C_{2-20}$ alkenyl that is unsubstituted or substituted by one or more substituents selected from the group consisting of:
-aryl;
-heteroaryl;
-heterocyclyl;.
—O—$C_{1-20}$ alkyl,
—O—($C_{1-20}$alkyl)$_{0-1}$-aryl;
—O—($C_{1-20}$alkyl)$_{0-1}$-heteroaryl;
—O—($C_{1-20}$alkyl)$_{0-1}$-heterocyclyl;
—$C_{1-20}$ alkoxycarbonyl;
—S(O)$_{0-2}$—$C_{1-20}$ alkyl;
—S(O)$_{0-2}$—($C_{1-20}$ alkyl)$_{0-1}$-aryl;
—S(O)$_{0-2}$—($C_{1-20}$ alkyl)$_{0-1}$-heteroaryl ;
—S(O)$_{0-2}$—($C_{1-20}$ alkyl)$_{0-1}$-heterocyclyl;
—N($R_{310}$)$_2$;
—$N_3$;
oxo;
-halogen;
—$NO_2$;
—OH; and
—SH; and
—$C_{1-20}$ alkyl-N$R_{310}$-Q-X—$R_{410}$ or —$C_{2-20}$ alkenyl-N$R_{310}$-Q-X—$R_{410}$ wherein Q is —CO— or —$SO_2$—; X is a bond, —O— or —N$R_{310}$— and $R_{410}$ is aryl; heteroaryl; heterocyclyl; or —$C_{1-20}$ alkyl or $C_{2-20}$ alkenyl that is unsubstituted or substituted by one or more substituents selected from the group consisting of:
-aryl;
-heteroaryl;
-heterocyclyl;
—O—$C_{1-20}$ alkyl,
—O—($C_{1-20}$alkyl)$_{0-1}$-aryl;
—O—($C_{1-20}$alkyl)$_{0-1}$-heteroaryl;
—O—($C_{1-20}$alkyl)$_{0-1}$-heterocyclyl;
—$C_{1-20}$ alkoxycarbonyl;
—S(O)$_{0-2}$—$C_{1-20}$ alkyl;
—S(O)$_{0-2}$—($C_{1-20}$ alkyl)$_{0-1}$-aryl;
—S(O)$_{0-2}$—($C_{1-20}$ alkyl)$_{0-1}$-heteroaryl
—S(O)$_{0-2}$—($C_{1-20}$ alkyl)$_{0-1}$-heterocyclyl;
—N($R_{310}$)$_2$;
—N$R_{310}$—CO—O—$C_{1-20}$alkyl;
—$N_3$;
oxo;
-halogen;
—$NO_2$;
—OH; and
—SH; or $R_{410}$ is wherein Y is —N— or —CR—;
$R_{210}$ is selected from the group consisting of:
-hydrogen;
—$C_{1-10}$ alkyl;
—$C_{2-10}$ alkenyl;
-aryl;
—$C_{1-10}$ alkyl —O—$C_{1-10}$-alkyl;
—$C_{1-10}$ alkyl-O—$C_{2-10}$ alkenyl; and
—$C_{1-10}$ alkyl or $C_{2-10}$ alkenyl substituted by one or more substituents selected from the group consisting of:
—OH;
-halogen;,
—N($R_{310}$)$_2$;
—CO—N($R_{310}$)$_2$;
—CO—$C_{1-10}$ alkyl;
—$N_3$;
-heteroaryl;
-heterocyclyl;
—CO-aryl; and
—CO-heteroaryl;
each $R_{310}$ is independently selected from the group consisting of hydrogen and $C_{1-10}$ alkyl; and each R is independently selected from the group consisting of hydrogen, $C_{1-10}$ alkyl, $C_{1-10}$ alkoxy, halogen and trifluoromethyl, and pharmaceutically acceptable salts thereof.

XI wherein
B is —NR—C(R)$_2$—C(R)$_2$—; —C(R)$_2$—NR—C(R)$_2$—C(R)$_2$—; —C(R)$_2$—C(R)$_2$—NR—C(R)$_2$— or —C(R)$_2$—C(R)$_2$—C(R)$_2$—NR—;

$R_{111}$ is selected from the group consisting of:
-hydrogen;
—$C_{1-20}$ alkyl or $C_{2-20}$ alkenyl that is unsubstituted or substituted by one or more substituents selected from the group consisting of:
-aryl;
-heteroaryl;
-heterocyclyl;
—O—$C_{1-20}$ alkyl;
—O—($C_{1-20}$alkyl)$_{0-1}$-aryl;
—O—($C_{1-20}$alkyl)$_{0-1}$-heteroaryl;
—O—($C_{1-20}$alkyl)$_{0-1}$-heterocyclyl;
—$C_{1-20}$ alkoxycarbonyl;
—S(O)$_{0-2}$—$C_{1-20}$ alkyl;
—S(O)$_{0-2}$—($C_{1-20}$ alkyl)$_{0-1}$-aryl;
—S(O)$_{0-2}$—($C_{1-20}$ alkyl)$_{0-1}$-heteroaryl;
—S(O)$_{0-2}$—($C_{1-20}$ alkyl)$_{0-1}$-heterocyclyl;
—N($R_{311}$)$_2$;
—N$_3$;
oxo;
-halogen;
—NO$_2$;
—OH; and
—SH; and
—$C_{1-20}$ alkyl-NR$_{311}$-Q-X—R$_{411}$ or —$C_{2-20}$ alkenyl-NR$_{311}$-Q-X—R$_{411}$ wherein Q is —CO— or —SO$_2$; X is a bond, —O— or —NR$_{311}$— and R$_{411}$ is aryl; heteroaryl; heterocyclyl; or —$C_{1-20}$ alkyl or $C_{2-20}$ alkenyl that is unsubstituted or substituted by one or more substituents selected from the group consisting of:
-aryl;
-heteroaryl;
-heterocyclyl;
—O—$C_{1-20}$ alkyl,
—O—($C_{1-20}$alkyl)$_{0-1}$-aryl;
—O—($C_{1-20}$alkyl)$_{0-1}$-heteroaryl;
—O—($C_{1-20}$alkyl)$_{0-1}$-heterocyclyl;
—$C_{1-20}$ alkoxycarbonyl;
—S(O)$_{0-2}$—$C_{1-20}$ alkyl;
—S(O)$_{0-2}$—($C_{1-20}$ alkyl)$_{0-1}$-aryl;
—S(O)$_{0-2}$—($C_{1-20}$ alkyl)$_{0-1}$-heteroaryl;
—S(O)$_{0-2}$—($C_{1-20}$ alkyl)$_{0-1}$-heterocyclyl;
—N($R_{311}$)$_2$;
—NR$_{311}$—CO—O—$C_{1-20}$alkyl;
—N$_3$;
oxo;
-halogen;
—NO$_2$;
—OH; and
—SH; or $R_{411}$ is wherein Y is —N— or CR—;
$R_{211}$ is selected from the group consisting of:
-hydrogen;
—$C_{1-10}$ alkyl;
—$C_{2-10}$ alkenyl;
-aryl
—$C_{1-10}$ alkyl-O—$C_{1-10}$-alkyl
—$C_{1-10}$ alkyl-O—$C_{2-10}$ alkenyl, and
—$C_{1-10}$ alkyl or $C_{2-10}$ alkenyl substituted by one or more substituents selected from the group consisting of:
—OH;
-halogen;
—N($R_{311}$)$_2$;
—CO—N($R_{311}$)$_2$;
—CO—$C_{1-10}$ alkyl;
—N$_3$;
-aryl;
-heteroaryl;
-heterocyclyl;
—CO-aryl; and
—CO-heteroaryl;
each $R_{311}$ is independently selected from the group consisting of hydrogen and $C_{1-10}$ alkyl; and
each R is independently selected from the up consisting of hydrogen, $C_{1-10}$ alkyl, $C_{1-10}$ alkoxy, halogen and trifluoromethyl,
and pharmaceutically acceptable, salts thereof.

Additional preferred 1H-imidazo[4,5-c]quinolin-4-amines and tetrahydro-1H-imidazo[4,5-c]quinolin-4-amines include compounds defined by Formulas XII, XIII and XIV below:

XII wherein
$R_{112}$ is -alkyl-NR$_{312}$—CO—R$_{412}$ or -alkenyl-NR$_{312}$—CO—R$_{412}$ wherein R$_{412}$ is aryl, heteroaryl, alkyl or alkenyl, each of which may be unsubstituted or substituted by one or more substituents selected from the group consisting of:
-alkyl;
-alkenyl;
-alkynyl;
-(alkyl)$_{0-1}$-aryl;

-(alkyl)$_{0-1}$-(substituted aryl);
-(alkyl)$_{0-1}$-heteroaryl;
-(alkyl)$_{0-1}$-(substituted heteroaryl);
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-substituted heteroaryl);
—CO-aryl;
—CO-(substituted aryl);
—CO-heteroaryl;
—CO-(substituted heteroaryl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—P(O)(OR$_{312}$)$_2$;
—NR$_{312}$—CO—O-alkyl ;
—N$_3$;
-halogen;
—NO$_2$;
—CN;
-haloalkyl;
—O-haloalkyl;
—CO-haloalkyl;
—OH;
SH; and in the case of alkyl, alkenyl or heterocyclyl, oxo; or R$_{412}$ is wherein R$_{512}$ is an aryl, (substituted aryl), heteroaryl, (substituted heteroaryl), heterocyclyl or (substituted heterocyclyl) group;
R$_{212}$ is selected from the group consisting of:
-hydrogen;
-alkyl;
-alkenyl;
-aryl;
-(substituted aryl);
-heteroaryl;
-(substituted heteroaryl);
-heterocyclyl;
-(substituted heterocyclyl);
-alkyl-O-alkyl,
-alkyl-O-alkenyl; and
-alkyl or alkenyl substituted by one or more substituents selected from the group consisting of:
　—OH ;
　-halogen;
　—N(R$_{312}$)$_2$;
　—CO—N(R$_{312}$)$_2$;
　—CO—C$_{1-10}$ alkyl;
　—CO—O—C$_{1-10}$ alkyl;
　—N$_3$;
　-aryl;
　-(substituted aryl);
　-heteroaryl;
　-(substituted heteroaryl);
　-heterocyclyl;
　-(substituted heterocyclyl);
　—CO-aryl; and
　—CO-heteroaryl;
each R$_{312}$ is independently selected from the group consisting of hydrogen; C$_{1-10}$ alkyl-heteroaryl; C$_{1-10}$ alkyl-(substituted heteroaryl); C$_{1-10}$ alkyl-aryl; C$_{1-10}$ alkyl-(substituted aryl) and C$_{1-10}$ alkyl;
v is 0 to 4;
and each R$_{12}$ present is independently selected from the group consisting of C$_{1-10}$ alkyl, C$_{1-10}$ alkoxy, halogen and trifluoromethyl;

XIII wherein
R$_{113}$ is -alkyl-NR$_{313}$—SO$_2$—X—R$_{413}$ or -alkenyl-NR$_{313}$—SO$_2$—X—R$_{413}$;
X is a bond or —NR$_{513}$—;
R$_{413}$ is aryl, heteroaryl, heterocyclyl, alkyl or alkenyl, each of which may be unsubstituted or substituted by one or more substituents selected from the group consisting of:
-alkyl;
-alkenyl;
-aryl;
-heteroaryl;
-heterocyclyl;
-substituted cycloalkyl;
-substituted aryl;
-substituted heteroaryl;
-substituted heterocyclyl;
—O-alkyl;
—O-(alkyl)$_{0-1}$-aryl;
—O-(alkyl)$_{0-1}$-substituted aryl;
—O-(alkyl)$_{0-1}$-heteroaryl;;
—O-(alkyl)$_{0-1}$-substituted heteroaryl;
—O-(alkyl)$_{0-1}$-heterocyclyl;
—O-(alkyl)$_{0-1}$-substituted heterocyclyl;
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-substituted aryl;
—S(O)$_{0-2}$-(alkyl)$_{0-1}$-heteroaryl;
—S(O)$_{0-2}$-(alkyl)$_{0-1}$-substituted heteroaryl;
—S(O)$_{0-2}$-(alkyl)$_{0-1}$-heterocyclyl;
—S(O)$_{0-2}$-(alkyl)$_{0-1}$-substituted heterocyclyl;
-(alkyl)$_{0-1}$-NR$_{313}$R$_{313}$;
-(alkyl)$_{0-1}$-NR$_{313}$—CO—O-alkyl;
-(alkyl)$_{0-1}$-NR$_{313}$—CO-alkyl;
-(alkyl)$_{0-1}$-NR$_{313}$—CO-aryl;
-(alkyl)$_{0-1}$-NR$_{313}$—CO-substituted aryl;
-(alkyl)$_{0-1}$-NR$_{313}$—CO-heteroaryl;
-(alkyl)$_{0-1}$-NR$_{313}$—CO-substituted heteroaryl;
—N$_3$;
-halogen;

-haloalkyl;
-haloalkoxy;
—CO-haloalkyl;
—CO-haloalkoxy;
—$NO_2$;
—CN;
—OH;
—SH; and in the case of alkyl, alkenyl, or heterocyclyl, oxo;
$R_{213}$ is selected from the group consisting of:
-hydrogen;
-alkyl;
-alkenyl;
-aryl;
-substituted aryl;
-heteroaryl;
-substituted heteroaryl;
-alkyl-O-alkyl;
-alkyl-alkenyl; and
-alkyl or alkenyl substituted by one or more substituents selected from the group consisting of:
—OH;
-halogen;
—$N(R_{313})_2$;
—CO—$N(R_{313})_2$;
—CO—$C_{1-10}$ alkyl;
—CO—O—$_{C1-10}$ alkyl;
—$N_3$;
-aryl;
-substituted aryl;
-heteroaryl;
-substituted heteroaryl;
-heterocyclyl;
-substituted heterocyclyl;
—CO-aryl;
—CO-(substituted aryl);
—CO-heteroaryl; and
—CO-(substituted heteroaryl);
each $R_{313}$ is independently selected from the group consisting of hydrogen and $C_{1-10}$ alkyl;
$R_{513}$ is selected from the group consisting of hydrogen and $C_{1-10}$ alkyl, or $R_{413}$ and $R_{513}$ can combine to form a 3 to 7 membered heterocyclic or substituted heterocyclic ring;
v is 0 to 4 and each $R_{13}$ present is independently selected from the group consisting of $C_{1-10}$ alkyl, $C_{1-10}$ alkoxy, halogen and trifluoromethyl;

XIV wherein
$R_{114}$ is alkyl-$NR_{413}$—CY—$NR_{514}$—X—$R_{414}$ or -alkenyl-$NR_{314}$—CY—$NR_{514}$—X—$R_{414}$
wherein
Y is =O or =S;
X is a bond, —CO— or —$SO_2$—;

$R_{414}$ is aryl, heteroaryl, heterocyclyl, alkyl or alkenyl, each of which may be unsubstituted or substituted by one or more substituents selected from the group consisting of:
alkyl;
-alkenyl;
-aryl;
-heteroaryl;
-heterocyclyl;
-substituted aryl;
-substituted heteroaryl;
-substituted heterocyclyl;
—O-alkyl;
—O-(alkyl)$_{0-1}$-aryl;
—O-(alkyl)$_{0-1}$-substituted aryl;
—O-(alkyl)$_{0-1}$-heteroaryl;
—O-(alkyl)$_{0-1}$-substituted heteroaryl;
—O-(alkyl)$_{0-1}$-heterocyclyl;
—O-(alkyl)$_{0-1}$-substituted heterocyclyl;
—COOH;
—CO—O-alkyl;
—CO-alkyl;
—$S(O)_{0-2}$-alkyl;
—$S(O)_{0-2}$-(alkyl)$_{0-1}$-aryl;
—$S(O)_{0-2}$-(alkyl)$_{0-1}$-substituted aryl;
—$S(O)_{0-2}$-(alkyl)$_{0-1}$-heteroaryl; ,
—$S(O)_{0-2}$-(alkyl)$_{0-1}$-substituted heteroaryl;
—$S(O)_{0-2}$-(alkyl)$_{0-1}$-heterocyclyl;
—$S(O)_{0-2}$-(alkyl)$_{0-1}$-substituted heterocyclyl;
-(alkyl)$_{0-1}$-$NR_{314}R_{314}$;
-(alkyl)$_{0-1}$-$NR_{314}$—CO—O-alkyl;
-(alkyl)$_{0-1}$-$NR_{314}$—CO-alkyl;
-(alkyl)$_{0-1}$-$NR_{314}$—CO-aryl;
-(alkyl)$_{0-1}$-$NR_{314}$—CO-substituted aryl;
-(alkyl)$_{0-1}$-$NR_{314}$—CO-heteroaryl;
-(alkyl)$_{0-1}$-$NR_{314}$—CO-substituted heteroaryl;
—$N_3$;
-halogen;
-haloalkyl;
-haloalkoxy;
—CO-haloalkoxy;
—$NO_2$;
—CN;
—OH;
—SH; and, in the case of alkyl, alkenyl or heterocyclyl, oxo; with the proviso that when X is a bond $R_{414}$ can additionally be hydrogen;
$R_{214}$ is selected from the group consisting of:
-hydrogen;
-alkyl;
-alkenyl;
-aryl;
-substituted-aryl;.
-heteroaryl;
-substituted heteroaryl;
-alkyl-O-alkyl;
-alkyl-O-alkenyl; and
-alkyl or alkenyl substituted by one or more substituents selected from the group consisting of:
—OH;
-halogen;
—$N(R_{314})_2$;
—CO—$N(R_{314})_2$;
—CO—$C_{1-10}$ alkyl;
—CO—O—$C_{1-10}$ alkyl;
—$N_3$;
-aryl;
-substituted aryl;

-heteroaryl;
-substituted heteroaryl;
-heterocyclyl;
-substituted heterocyclyl;
—CO-aryl;
—CO-(substituted aryl);
—CO-heteroaryl; and
—CO-(substituted heteroaryl);

each $R_{314}$ is independently selected from the group consisting of hydrogen and $C_{1-10}$ alkyl;

$R_{514}$ is selected from the group consisting of hydrogen and $C_{1-10}$ alkyl, or $R_{414}$ and $R_{514}$ can combine to form a 3 to 7 membered heterocyclic or substituted heterocyclic ring;

v is 0 to 4 and each $R_{14}$ present is independently selected from the group consisting of $C_{1-10}$ alkyl, $C_{1-10}$ alkoxy, halogen and trifluoromethyl, and a pharmaceutically acceptable salts thereof.

Particularly preferred compounds include 1-(2-methylpropyl)-1H-imidazo[4,5-c]quinolin-4-amine (imiquimod), 4amino-2-ethoxymethyl-α,α-dimethyl-1H-imidazo[4,5-c]quinoline-1-ethanol (resiquimod), 2-propyl[1,3]thiazolo[4,5-c]quinolin-4-amine, N-[4-(4-amino-2-butyl-1H-imidazo[4,5c][1,5]naphthyridin-1-yl)butyl]-N'-cyclohexylurea; 2-methyl-1-(2-methylpropyl)-1H-imidazo[4,5-c][1,5]naphthyridin-4-amine, and 1-(2-methylpropyl)-1H-imidazo[4,5-c][1,5]naphthyridin-4-amine.

The pharmaceutical compositions can be provided in a form suitable for systemic application or in a form suitable for local delivery to the affected site. The latter mode is presently preferred. The pharmaceutical compositions can be formulated to provide for delivery of the IRM compound to the treatment site at a predetermined rate, for a predetermined duration, alone, or in combination with other therapeutic or prophylactic agents, for example antibiotics, fluoride sources etc. Excipients commonly used to formulate drugs into a suitable vehicle can be incorporated as necessary provided that the excipient does not substantially interfere with the function or stability of the composition. Non-limiting examples of forms suitable for the pharmaceutical compositions include enhanced viscosity formulations such as disclosed in U.S. Pat. Nos. 5.939,047 and 6,123,957; transmucosal patches such as disclosed in U.S. Pat. Nos. 5,780,045 and 5,750,134 and PCT Publication WO 00/19987; microcapsules such as disclosed in U.S. Pat. No. 5,500,228; biodegradable cross-linked hydrolyzed gelatin matrices such as those used in the PerioChip™ (available from Perio Products Ltd., Jerusalem, Israel); dental rinses and dentifrices. Excipients such as flavorings, colorants, surfactants, binders can be employed as needed.

A "treatment site" means the site where the pharmaceutical composition is delivered to the patient. Treatment sites are typically local sites proximate to a lesion and generally include the gingival surfaces, periodontal pockets, or any other site that the drug could be delivered to the maxillary or mandibular tissue. The composition is typically delivered topically or by placing the composition in the subgingival space (periodontal pocket).

As used herein, the term "therapeutically effective amount" means an amount of an IRM compound sufficient to prevent, reduce or reverse periodontal disease. The therapeutically effective amount of an IRM compound for periodontitis will vary depending on such things as the activity of the particular compound, the particular composition administered, the duration of delivery, the frequency of administration, the treatment site, and any other therapeutic agents being coadministered.

In general, a pharmaceutical composition useful for practicing the methods of the invention can contain from about 0.001% to 5.0% of an IRM compound based on total weight of the pharmaceutical composition. Typically the composition will contain from about 0.01% to 1% of an IRM compound.

The IRM compound may be present in the pharmaceutical composition as the sole therapeutically active ingredient or in combination with other therapeutic agents such as antibiotics, e.g., penicillins, tetracycline; antiseptics, e.g., chlorhexidine; corticosteroids, e.g., hydrocortisone, betamethasone; nonsteroidal antiinflammatories, e.g., flurbiprofen, ibuprofen, naproxen.

The frequency and duration of administration can vary as needed for prevention or treatment of the disease. Treatment regimens may include administration at least one time per week, typically two to three times per week, or even daily for at least one week, typically two weeks and in some cases three to four weeks. The patient can be rechecked according to the common standards of care. Thus recalls can be monthly, every two months and typically every three months. Repeated administration can be provided as needed.

Typically, the IRM compound can be applied to a treatment site in some type of sustained release formulation, such as gels, capsules, patches, biodegradable matrices, etc. for delivery of the IRM compound to the treatment site over a period of about 1–24 hours, typically about 1–8 hours, and in some embodiments, about 1–3 hours. It is also foreseen that in certain situations, a burst of IRM compound can be provided by directs administration, such as by subgingival placement, use of a dentifrice or mouth wash, etc. at the discretion of the clinician.

The following Examples are provided to further explain the invention through specific description of some embodiments of the invention. The Examples, however, are not intended to limit the scope of the invention.

EXAMPLE 1

Treatment of Mice with an IRM

Studies in mice infected with bacteria known to cause periodontitis were performed to determine the potential utility of the IRM compounds in this disease.

Preparation and Maintenance of Bacterial Cultures

An isolate of *Porphyromonas gingivalis* from the subgingival pocket of a patient with adult periodontitis and non-insulin dependent diabetes was used. The isolate is deposited with American Type Culture Collection, 10801 University Blvd., Manassas, Va. 20110-2209 USA as ATCC Accession No. 53977 (strain A7A1-28). The organisms were propagated in an anaerobic jar (Becton Dickinson Microbiology Systems, Cockeysville, Md.) under an atmosphere of 5% $CO_2$ 10% $H_2$ and 85% $N_2$ at 37° C. on PRAS (prereduced anaerobically sterilized) Brucella agar plates (Anaerobe Systems, Morgan Hill, Calif.). Broth cultures were grown in BHTS media, a 50% mixture of Tripticase Soy and Brain Heart Infusion broth supplemented with 5% Yeast Extract (all from Becton Dickinson Microbiology Systems), 10 μg/L hemin, 1 μg/L metadione and 5% horse serum (Sigma Chemical, St. Louis. Mo.). Species were maintained by weekly transfer on plates. Frozen stocks were made by re-suspending log-phase cultures in 15% glycerol in BHTS and maintaining at −70° C. for several months.

Oral Infection of Mice with *Porphyromonas gingivalis*

90 conventional BALB/c specific pathogen-free mice (Charles River Labs, Wilmington, Mass.) were divided into three groups of about 30 mice per group. As shown in Table 1, Groups II and III, but not I, were infected with *P. gingivalis* as described below. Groups I and II were administered an IRM compound as described below.

TABLE 1

Experimental Protocol

| Group/Treatment | Infected with *P. gingivalis* |
|---|---|
| I/IRM | NO |
| II/IRM | YES |
| III/NONE | YES |

All mice were kept in an animal colony, where they were caged away from other animals. All mice were kept on a 12-hour light/dark cycle and received distilled water ad libitum. Mice within experiments were sex- and age-matched (12–18 weeks at the start of various experiments).

The mice in Groups I–III were given sulphamethoxazole/trimethoprim, 10 ml per pint in deionized water, ad libitum for 10 days before experimentation, followed by 4 days without antibiotics. The mice of Groups II–III were then infected by gavage with $10^9$ colony-forming units of live *P. gingivalis*, in 100 μl of phosphate buffered saline (PBS) with 2% carboxymethylcellulose, three times at 2 to 4 day intervals as described in Klausen et al, "Two complementary methods of assessing periodontal bone level in rats", *Scandinavian Journal of Dental Research*, 97, 494–9 (1989).

Figure 2:
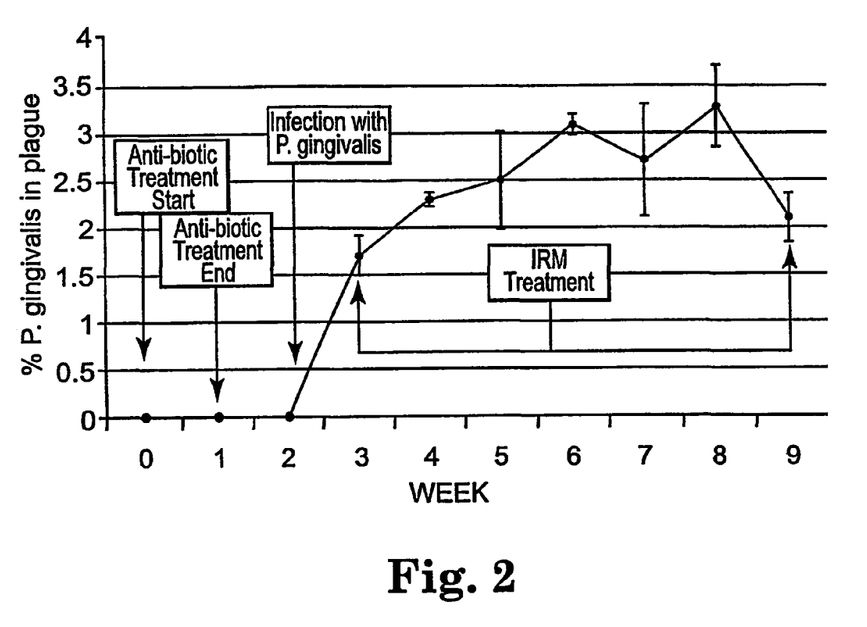
FIG. 2 is a graph showing the proportion of *Porphyromonas gingivalis* in the plaque of infected mice.

As shown in FIG. 2, two weeks prior to infection there was no evidence of *P. gingivalis* in any of the subject animals, a result that continued up to infection. The proportion of *P. gingivalis* in samples collected the first week after infection reached about 2%. See below. It remained between 2% and 5% during the remainder of the experiment. There was no significant difference between the levels of *P. gingivalis* in the IRM treated or untreated animals at any point in the experiment.

Bacterial Isolation from Plague of Infected Mice

Subgingival plaque samples were obtained from the molars of nice from all three groups using sterile fine paper points (Johnson and Johnson Dental Products Co. East Windsor, N.J.). The points were placed in 1 ml of water that was then tested for total bacteria and *P. gingivalis* levels by quantitative PCR similar to that described for *Bacteroides forsythus* in Shelburne et al, "Quantitation of *Bacteroides forsythus* in subgingival plaque: comparison of immunoassay and quantitative polymerase chain reaction", *J. Microbial. Methods*, 39:97–107 (2000).

Treatment with Resiquimod

The mice of Groups I and II were dosed by oral gavage twice weekly for seven weeks with either 1 mg/kg or 0.1 mg/kg of resiquimod (4-amino-2-ethoxymethyl-α,α-dimethyl-1H-imidazo[4,5-c]quinoline-1-ethanol) in 100 μl of PBS. Animals were sacrificed at 43 days after treatment began.

Measurement of Alveolar Bone Loss

Bone loss around the maxillary molars was assessed by a morphometric method developed for studies of bone loss in mice. Baker P J., et al., "Oral infection with *Porphyromonas gingivalis* and induced alveolar bone loss in immunocompetent and severe combined immunodeficient mice," *Arch. Oral Biol.*, 39(12):1035–40 (December 1994). Jaws were de-fleshed after a 5-minute treatment in boiling water at 15 p.s.i. (1.05 Kg/cm²), immersed overnight in 3% hydrogen peroxide, air-dried and stained with 1% methylene blue. The bone level, that is, the distance from the cemento-enamel junction (CBJ) to the alveolar bone crest on the maxillary molars, was measured under a dissecting microscope (×30). Fourteen (14) measurements of the bone level were made per mouse. All measurements of bone level were done three times in a random fashion. Values for horizontal bone levels in μm per site were generated by computer analysis of calibrated lines from the CEJ to the alveolar bone crest image acquired by video camera.

Results

Figure 3:
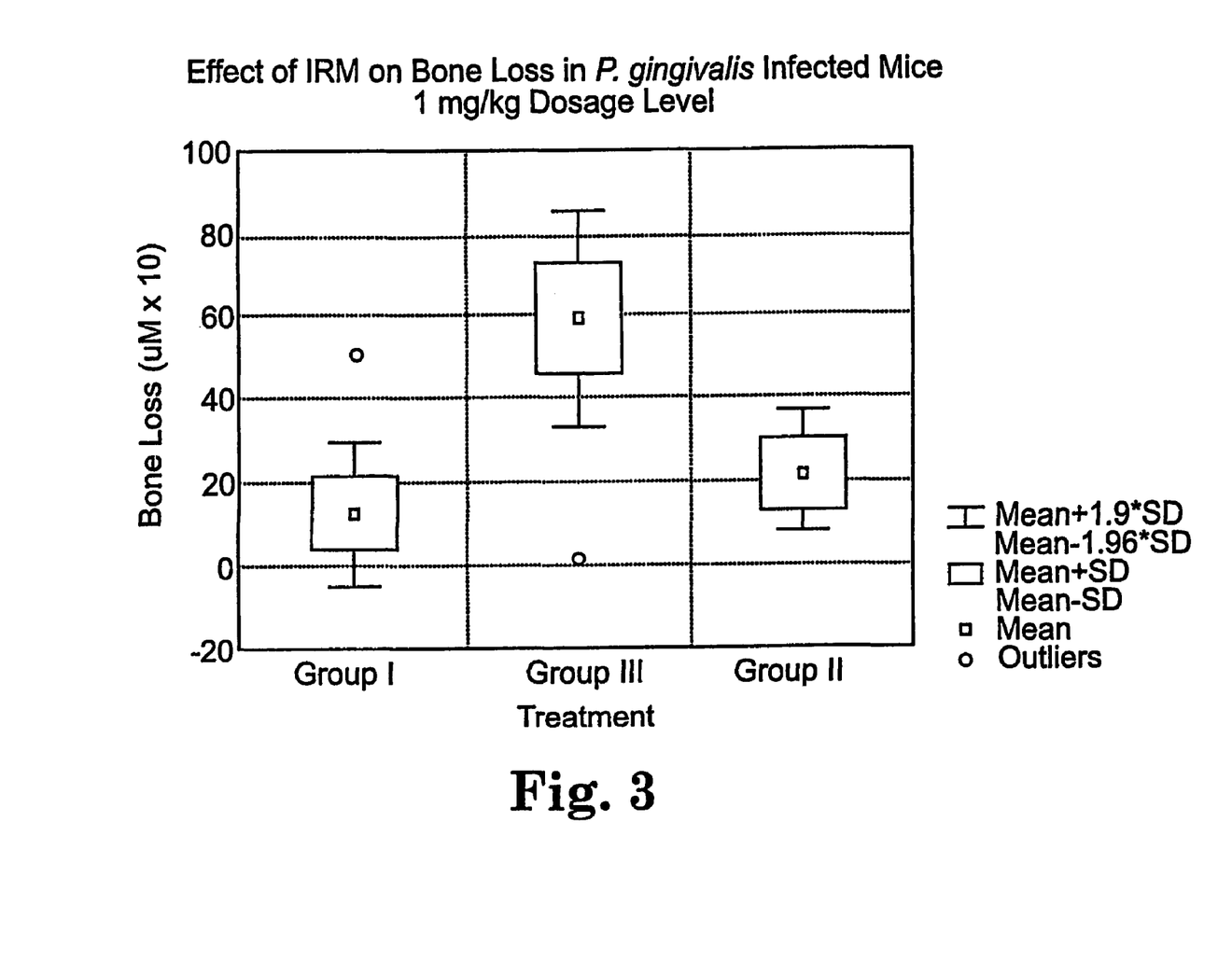
FIG. 3 is a graph showing bone loss in infected mice.

In animals treated with resiquimod there was substantially less bone loss than in untreated animals (FIG. 3), and the difference was significant at a level appropriate for this model (p<0.01). There was no difference between the animals treated with 1 mg/kg doses of resiquimod and those treated with 0.1 mg/kg.

Interestingly, there was no reduction in the levels of *P. gingivalis* in the plaque of the subject animals that correlated with the difference in bone loss or the treatment (or non-treatment) of the mice. This indicates that the reduction in bone loss is due to modification of some host response, not the elimination of the bacteria, although they are clearly required to initiate the disease.

EXAMPLE 2

Treatment of Naturally Occurring Periodontal Disease in a Dog with an IRM Gel Compostion One dog with naturally occurring periodontal disease was identified by clinical signs including Gingival Index (scored 0–3 by observation), Bleeding Index (scored 0–3 by observation), and Probing Depth (measured to the nearest mm using a North Carolina Probe). The animal was treed with a gel composition containing resiquimod, prepared as described below, in addition to the standard treatment of scaling and root planing. Therapeutic efficacy was determined by a trained examiner measuring the aforementioned indicies around the affected teeth.

Preparation of IRM Gel Composition Containing the IRM Resiquimod

Propylene glycol (700 g) and the IRM resiquimod (4-amino-2-ethoxymethyl-α,α-dimethyl-1H-imidazo[4,5-c]quinoline-1-ethanol, 7.0 g) were added to a 1000 mL glass beaker. The resulting mixture was heated (about 56° C.) with stirring until all of the resiquimod was dissolved. The resulting solution was added to the mixing bowl of a ROSS LDM-4 mixer. Triacetin (11,963.0 g) was added to the mixing bowl and the resulting mixture was mixed for 10 minutes at 36 rpm. Colloidal silicon dioxide (1,330.0 g, AEROSIL® 200 from Degussa, Frankfurt, Germany) was added in five parts. After each addition the resulting mixture was mixed at ambient pressure for 1 to 2 minutes at 36 rpm and then under vacuum (about 18 in Hg; $4.0 \times 10^4$ Pa) for about 9 minutes at 36 rpm. The sides of the mixing bowl and the mixing blades were scraped. The formulation was mixed under vacuum (about 17 in Hg; $4.3 \times 10^4$ Pa) for about 10 minutes at 36 rpm. The resulting gel contained 0.05% resiquimod, 5.0% propylene glycol, 9.5% colloidal silicon dioxide, and 85.45% triacetin.

Treatment with an IRM Gel Composition

The animal was sedated with xylazine at a dose of about 1 mg/kg and its teeth cleaned of supragingival and subgingival plaque. The teeth affected by periodontitis were scaled and root planed to remove plaque and calculus from both supragingival (enamel) and subgingival (root) tooth surfaces using an ultrasonic Cavitron® (Dentsply, York, Pa.) and curets. The Cavitron was used to remove gross debris and the curets were used to smooth the root surface. A clean, smooth root surface resulting from the root planing allows epithelial and connective tissue attachment to the root surface during the healing process.

During the scaling procedure, there was no deliberate attempt to remove tooth substance along with the calculus. Root planing was performed to remove residual embedded calculus and portions of cementum from the roots of the teeth to produce a smooth, hard, clean surface. The primary objective of scaling and root planing is to restore gingival health by completely removing material from the tooth surface that provokes gingival inflammation; that is, plaque, calculus and altered cementum. Scaling and root planing were not done as separate procedures in this Example. The difference between scaling and root planing is only a matter of degree. The nature of the tooth surface determines the degree to which the root surface is scaled or planed.

Depending on the size of the periodontitis lesion, about 10–50 μl of the resiquimod gel composition prepared as described above was applied to sites affected by periodontitis. The composition was placed in the periodontal pocket adjacent to each site using a blunt 27 ga. needle and syringe filled with the composition. In this example a single application of the gel was used.

After treatment the animal was treated with yohimbine at about 0.1 mg/kg to reverse the sedation and the animal was returned to its cage.

Clinical Measurements

The pockets were examined at weekly intervals for the indicies measured at the time of treatment. Measurement of attachment loss was performed using a standard North Carolina Periodontal probe marked at 1 mm intervals. The probe, which is about 1 mm in diameter was inserted into the periodontal pocket to the base. The depth of the pocket (PD) was noted and the probe was withdrawn. The depth of the probe was noted at this time. At the same time the gingival index (GI) a measure of the redness of the gingival tissue (0=no redness to 3=very red, distended) was noted along with the bleeding index (BI) which is a measurement of the tendency of the pocket to bleed upon probing (0=no bleeding to 3=substantial bleeding). These are all standard measurements in dental practice for the evaluation of human periodontal disease.

Results

Figure 4A:
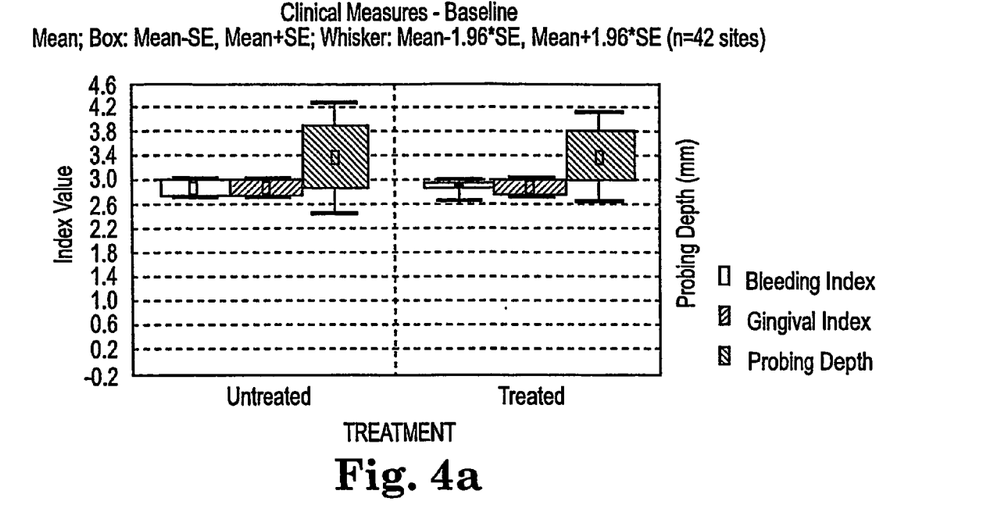
FIG. 4a is a graph of bleeding index, gingival index and probing depth of a dog pre-treatment.
Figure 4B:
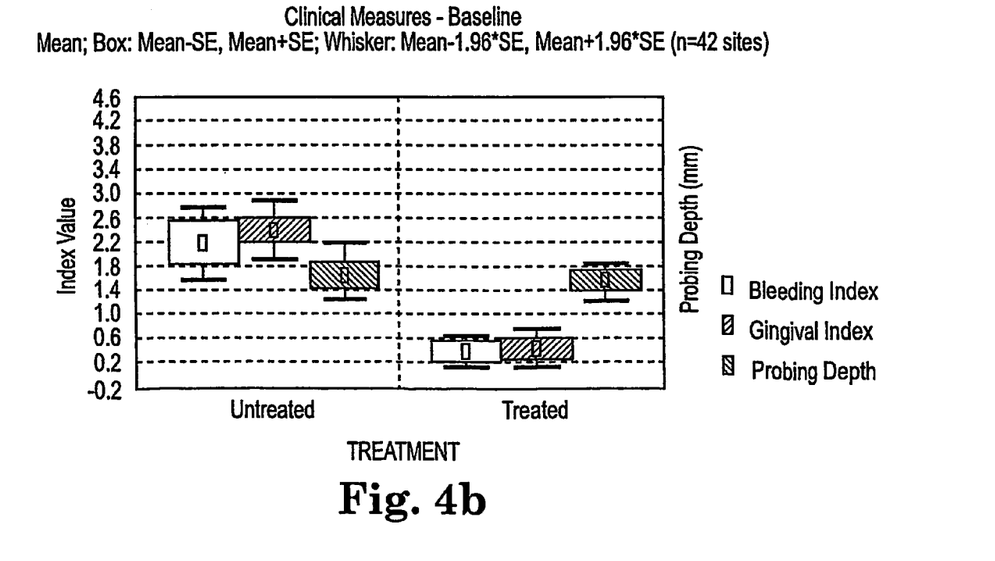
FIG. 4b is a graph of bleeding index, gingival index and probing depth of a dog at two weeks post-treatment.

Referring to FIGS. 4a and 4b, there was an over all improvement in PD, BI and GI as a result of the mechanical cleaning of the teeth (compare left hand panels of Baseline graph (FIG. 4a) and 2 Week Post-Treatment graph (FIG. 4b). There was improvement in the BI and GI of the treated sites compared to untreated sites that is statistically significant (p<0.01). (Compare left and right panels of the 2 Week Post-Treatment graph, FIG. 4b). This is due to the IRM treatment.

There was no significant difference in the PD of the treated compared to untreated sites (compare left and right panels of 2 Week Post-Treatment graph, FIG. 4b). The inventors believe this is due to two-weeks being an insufficient time post-treatment for rebuilding the tooth attachment cellular apparatus.

The study was not a terminal study and thus bone loss was not determined

EXAMPLE 3

Treatment of Chronic Adult Periodontal Disease in a Human Patient with an IRM Containing Transmucosal Patch A human patient affected with chronic adult periodontal disease can be identified by clinical signs typically including BI, GI, Probing Depth. The human can be treated with a transmucosal patch containing an IRM, prepared as described in Example 4 below, in addition to the standard treatment of scaling and root planing.

The patient's teeth can be cleaned of supragingival plaque. The teeth affected by periodontitis can be scaled and root planed to remove plaque and calculus from both supragingival and subgingival tooth surfaces using known instruments, such as, for example, an ultrasonic Cavitron and curets. The Cavitron is used to remove gross debris and the curets are used to smooth the root surface.

Depending on the size of the periodontitis lesion, a transmucosal patch containing about 0.05–1.0% of IRM per patch, prepared, for example, as described in Example 4 below, can be adhered to the patient's gingiva proximate the sites affected by periodontitis. The transmucosal patches can remain adhered to the gingiva for about 1–24 hours. In a typical situation the patch will remain adhered for about 1–3 hours. The patches can be applied two times a week for three weeks. The patient can be reexamined at 1 month after completion of treatment and at three month intervals thereafter.

Treatment can be repeated as necessary.

EXAMPLE 4

Preparation of a Transmucosal Patch Containing the IRM 4-amino-2-ethoxymethyl-α,α-dimethyl-1H-imidazo[4,5-c]quinoline-1-ethanol

A transmucosal patch suitable for gingival application was prepared containing the IRM compound 4-amino-2-ethoxymethyl-α,α-dimethyl-1H-imidazo[4,5-c]quinoline-1-ethanol (resiquimod).

Isooctyl acrylate (20.03 g), acrylic acid (19.98 g), methoxy polyethylene glycol 550 monomethacrylate (19.07 g), polyethylene glycol 400 diacrylate (0.72 g), polyacrylic acid (5.73 g of a solution containing 17.5% by weight of polyacrylic acid in water), polyoxyethylene 10 oleyl ether (21.78 g of Brij® 97), propylene glycol (10.00), water (2.89 g), resiquimod (0.10 g) and 2-hydroxy-1-(4-(2-hydroxyethoxy)phenyl)-2-methyl-1-propanone (0.55 g of Irgacure® 2959) were combined in a glass jar and then mixed on a platform shaker until a clear liquid composition was obtained. The composition contained 0.01% by weight of resiquimod.

The liquid was knife coated at a wet thickness of 25 mil (635 μM) onto the non-woven polypropylene side of a trilaminate backing and the exposed surface was covered with a clear polyester (1.5 mil, 38 μM) silicone coated release liner. The coated composition was then exposed to UVA light for 8 minutes so that the composition was exposed to a total energy of 2677 mJ/cm². The release liner was removed and the exposed surface of the cured compo-

What is claimed is:

1. A method of treating periodontitis by applying an immune response modifier (IRM) compound formulation directly to the periodontal pockets of a patient affected by periodontitis, wherein the IRM compound is of the formula wherein $R_{11}$ is selected from the group consisting of alkyl of one to ten carbon atoms, hydroxyalkyl of one to six carbon atoms, acyloxyalkyl wherein the acyloxy moiety is alkanoyloxy of two to four carbon atoms or benzoyloxy, and the alkyl moiety contains one to six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that if said benzene ring is substituted by two of said moieties, then said moieties together contain no more than six carbon atoms;

$R_{21}$ is selected from the group consisting of hydrogen, alkyl of one to eight carbon atoms, benzyl (phenyl)ethyl and phenyl, the benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that when the benzene ring is substituted by two of said moieties, then the moieties together contain no more than six carbon atoms; and each $R_1$ is independently selected from the group consisting of alkoxy of one to four carbon atoms, halogen, and alkyl of one to four carbon atoms, and n is an integer from 0 to 2, with the proviso that if n is 2, then said $R_1$ groups together contain no more than six carbon atoms.

2. The method according to claim 1 wherein the IRM is selected from the group consisting of 1-(2-methylpropyl)-1H-imidazo[4,5-c]quinolin-4-amine and 4-amino-2-ethoxymethyl-α,α-dimethyl-1H-imidazo[4,5-c]quinoline-1-ethanol.

3. The method according to claim 2 wherein the IRM is 4-amino-2-ethoxymethyl-(,(-1H-imidazo[4,5c]quinoline-1-ethanol.

4. The method according to claim 1 wherein the pharmaceutical formulation is in the form of a biodegradable matrix, a gel, a liquid, microcapsules, a mouth rinse, a paste, a semi-solid, a transmucosal patch or in a combination of these forms.

5. The method according to claim 1 wherein the pharmaceutical formulation is a gel formulation.

6. The method according to claim 1 wherein the periodontitis is chronic adult periodontitis.

7. The method according to claim 1 wherein the periodontitis is early onset periodontitis.

* * * * *